(12) United States Patent
Morita et al.

(10) Patent No.: US 8,506,697 B2
(45) Date of Patent: Aug. 13, 2013

(54) WATER-SOLUBLE AZO COMPOUND OR SALT THEREOF, INK COMPOSITION, AND COLORED BODY

(75) Inventors: Ryoutarou Morita, Tokyo (JP); Noriko Kajiura, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/634,798

(22) PCT Filed: Mar. 24, 2011

(86) PCT No.: PCT/JP2011/057111
§ 371 (c)(1),
(2), (4) Date: Sep. 13, 2012

(87) PCT Pub. No.: WO2011/122426
PCT Pub. Date: Oct. 6, 2011

(65) Prior Publication Data
US 2013/0011637 A1    Jan. 10, 2013

(30) Foreign Application Priority Data
Mar. 30, 2010    (JP) .................................. 2010-076832

(51) Int. Cl.
C09D 11/02      (2006.01)
C09B 33/12      (2006.01)
B41J 2/01        (2006.01)

(52) U.S. Cl.
USPC .......................... 106/31.48; 534/797; 347/100

(58) Field of Classification Search
USPC ... 106/31.48; 534/797; 347/100; 428/195.1
See application file for complete search history.

(56) References Cited

U.S. PATENT DOCUMENTS

| | | | |
|---|---|---|---|
| 5,622,550 A * | 4/1997 | Konishi et al. ............. | 106/31.48 |
| 6,867,286 B1 | 3/2005 | Holloway et al. | |
| 7,387,668 B2 * | 6/2008 | Kitayama et al. ......... | 106/31.48 |
| 7,740,696 B2 * | 6/2010 | Takahashi et al. ........ | 106/31.48 |
| 7,771,525 B2 * | 8/2010 | Morita et al. ............. | 106/31.48 |
| 7,951,234 B2 * | 5/2011 | Morita et al. ............. | 106/31.48 |
| 8,226,222 B2 * | 7/2012 | Kajiura et al. ............ | 347/100 |
| 8,425,676 B2 * | 4/2013 | Morita et al. ............. | 106/31.48 |
| 2005/0241527 A1 * | 11/2005 | Oshaughnessy et al. .. | 106/31.48 |
| 2009/0130399 A1 * | 5/2009 | Takahashi et al. ........ | 534/797 |
| 2011/0052885 A1 * | 3/2011 | Morita et al. ............. | 534/797 |
| 2011/0216117 A1 * | 9/2011 | Morita et al. ............. | 534/797 |
| 2012/0092400 A1 * | 4/2012 | Morita et al. ............. | 106/31.48 |

FOREIGN PATENT DOCUMENTS

| | | |
|---|---|---|
| JP | S60-260658 | 12/1985 |
| JP | S62-132969 | 6/1987 |
| JP | 2006-152244 | 6/2006 |
| JP | 2009-263514 | 11/2009 |
| JP | 2011-105798 | 6/2011 |
| WO | WO 2007/020719 | 2/2007 |
| WO | WO 2008/053776 | 5/2008 |

* cited by examiner

*Primary Examiner* — Helene Klemanski
(74) *Attorney, Agent, or Firm* — Knobbe Martens Olson & Bear LLP

(57) ABSTRACT

A water-soluble azo compound represented by formula (1) or a salt thereof, and an ink composition containing the compound or salt. The ink composition has a chroma saturation and hue suitable for inkjet recording, and enables a material recorded therewith to have high fastness in various fields, in particular high ozone gas resistance, while enabling an image recorded therewith to have excellent storage stability and the like. In formula (1), Q represents a halogen atom; x represents an integer of 2 to 4; and the group A represents an amino group represented by the following formula (101). In formula (101), y represents an integer of 1 to 3.

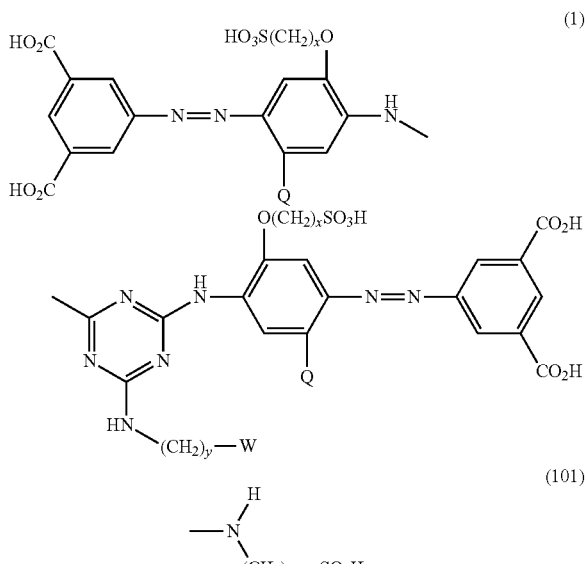

12 Claims, No Drawings

WATER-SOLUBLE AZO COMPOUND OR SALT THEREOF, INK COMPOSITION, AND COLORED BODY

This application is the U.S. National Phase under 35 U.S.C. §371 of International Application PCT/JP2011/057111, filed Mar. 24, 2011, designating the U.S., and published in Japanese as WO 2011/122426 on Oct. 6, 2011, which claims priority to Japanese Patent Application No. 2010-076832, filed Mar. 30, 2010, the entire contents of which are incorporated herein by reference.

TECHNICAL FIELD

The present invention relates to a water-soluble disazo compound or a salt thereof, an ink composition containing the same, and a colored body which was colored therewith.

BACKGROUND ART

For a recording method by an ink jet printer, which is one typical method among a variety of color recording methods, a variety of ink discharge systems have been developed. These systems execute recording by generating ink droplets, which are adhered onto any of a variety of record-receiving materials (e.g., paper, film, and fabric, etc.). According to this method, a recording head is not brought into direct contact with the record-receiving material; therefore, generation of noise can be avoided thus achieving silent recording. In addition, due to having the feature of reduced size, increased speed and coloring being readily achievable, prevalence in recent years has been in rapid progress, and thus great advancement hereafter is expected.

Inks containing a water-soluble coloring matter (dye) dissolved in an aqueous medium have been used as conventional inks for fountain pens, felt pens etc., and inks for ink jet recording. To these inks is generally added a water-soluble organic solvent in order to prevent pen tips or ink discharge nozzles from clogging with the ink. For these inks, performance such as ability to generate a recorded image with satisfactory density, probability of avoiding occurrence of clogging at the pen tips and nozzles, favorable drying characteristics on the record-receiving materials, suppression of bleeding, superior storage stability, and the like are in demand.

Clogging of nozzles of ink jet systems often results from hardening and deposition of a coloring matter when the moisture of the ink evaporates faster than other solvent and additives in the vicinity of the nozzle to cause a state of the composition including less moisture and a substantive amount of the solvent and additives. Therefore, one extremely important expected area of performance is that solids are less likely to be deposited even in the state in which the ink contains a low amount of moisture. On this ground, high solubility in the solvent and additives is also a property required for coloring matters. Also, in a known procedure for resolving a problem of clogging of nozzles, a coloring matter capable of providing a high print density is used. By using a coloring matter having a high print density, the content of the coloring matter in an ink can be reduced while maintaining a print density according to conventional procedures. This not only results in a reduction of the probability of deposition of the coloring matter, but also is advantageous in terms of costs, and thus development of a coloring matter having higher print density has been desired.

In the meantime, for recording image or character information on a color display of computers in full color by an ink jet printer, subtractive color mixing with four inks having different colors of, generally yellow (Y), magenta (M), cyan (C), and black (K) has been employed, whereby the recorded image is presented in full color. In order to reproduce an additive color mixing image formed with red (R), green (G), blue (B) on a CRT (cathode ray tube) display and the like as strictly as possible using subtractive color mixing, it is desired that Y, M and C, among the coloring matters used in inks, have a hue approximate to the standard color, and are brilliant. The term brilliance as herein referred to means, in general, to have a high chroma saturation. When three primary colors of Y, M and C having a low chroma saturation are used, narrowing occurs of the color region that can be expressed by a simple color or a mixed color, whereby the range of the color region to be expressed may be insufficient. Therefore, development of a coloring matter having a high chroma saturation, and an ink containing the same have been desired.

In addition, long term storage stability, as well as high density of the recorded image, and superior fastness such as water resistance, moisture resistance, light resistance and gas resistance of the image are also required properties for the inks. Herein, gas resistance means resistance to a phenomenon of causing discoloration and fading of a recorded image via a reaction of a gas present in the air and having an oxidizing action (also referred to as an oxidizing gas), with a coloring matter (dye) of the recorded image on or in the record-receiving material. Particularly, ozone gas among oxidizing gasses is considered as a main causative substance that promotes the discoloration and fading phenomenon of ink jet recorded images. Since this discoloration and fading phenomenon is characteristic in ink jet recorded images, improvement of the ozone gas resistance is a significant technical problem in the art.

Advancement of ink jet techniques in recent years has lead to a considerable increase in the speed of ink jet recording (printing). Thus, similarly to laser printers using an electronic toner, use of ink jet printers has started for printing of documents on plain paper which has a main application in office environments. Prevalence of the ink jet printers has been in progress particularly in small to medium scale office environments such as SOHO in particular, due to advantages such as no limitation of usable recording paper, and low cost of the printer itself. When an ink jet printer is thus used for applications in printing on plain paper, hue, color formation (print) density and water resistance tend to be regarded more importantly among qualities required for printed matter.

For the purpose of achieving these performances, a method in which a pigment ink is used was proposed. However, pigment inks do not have a state of solution as the coloring matter is not dissolved in an aqueous ink, but have a state of dispersion. Therefore, use of a pigment ink in ink jet recording may involve problems of stability of the ink per se, problems of clogging of nozzles of recording heads, and the like. In addition, when a pigment ink is used, a problem in connection with abrasion resistance often occurs. In the case of the dye inks, the aforementioned problems are reported to be comparatively less likely to occur; however, dye inks are significantly inferior particularly in water resistance as compared with pigment inks, and improvement of this disadvantage has been strongly desired. In addition, unlike pigment inks, dye inks are likely to involve problems of lowered coloring density as a result of faster permeation of the coloring matter adhered onto the surface of a plain paper by ink jet recording toward the back face direction of the paper.

In one method for attaining ink jet recorded images of photo image qualities, an ink receiving layer may be provided on the surface of a record-receiving material. In an ink receiving layer which is provided for such a purpose, a porous white inorganic substance is often included for facilitating drying of the ink and for minimizing bleeding of the coloring matter to provide high quality images. However, discoloration and fading due to ozone gas is markedly observed particularly on such a record-receiving material. Along with recent prevalence of digital cameras and color printers, the opportunity for printing images with photo image quality obtained by a digital camera or the like have increased also at home. Thus, discoloration and fading of the recorded image due to the oxidizing gas as described above has been a concern. With regard to yellow coloring matters, those having favorable resistance against oxidizing gas as well as light resistance have been proposed, as compared with others among three primary colors, i.e., magenta and cyan. However, yellow coloring matters for ink jet recording and yellow inks having high brilliance required for market, and also having various types of fastness properties that are sufficiently satisfactory have not yet been obtained.

As a well-known yellow coloring matter for ink jet that is superior in water solubility and brilliance, C. I. (Color Index) Direct Yellow 132 and Direct Yellow 142 are exemplified. Furthermore, a plurality of azo yellow coloring matters having superior fastness properties have been proposed on the basis of development of yellow coloring matters for ink jet recording in recent years.

Patent Document 1 discloses a water-soluble yellow azo compound having high solubility in water, moisture resistance and light resistance.

Patent Document 2 discloses a water-soluble yellow azo compound having high solubility in water, moisture resistance, ozone gas resistance, and light resistance.

Patent Document 3 discloses a water-soluble yellow azo compound having high solubility in water, moisture resistance, water resistance, ozone gas resistance, and light resistance.

Patent Document 4 discloses a water-soluble yellow azo compound having high solubility in water, moisture resistance, water resistance, ozone gas resistance, and light resistance.

Patent Document 1: U.S. Pat. No. 6,867,286
Patent Document 2: Japanese Unexamined Patent Application, Publication No. 2006-152244
Patent Document 3: WO 2008/053776
Patent Document 4: Japanese Unexamined Patent Application, Publication No. 2009-263514

DISCLOSURE OF THE INVENTION

Problems to be Solved by the Invention

An object of the present invention is to provide a water-soluble yellow coloring matter (compound) having high solubility in water, having superior balance between chroma saturation and ozone gas resistance. Another object of the present invention is to provide a yellow ink composition useful for various fields of recordings, particularly for ink jet recording, which yellow ink composition contains the yellow coloring matter.

Means for Solving the Problems

In order to solve the foregoing problems, the present inventors thoroughly investigated, and consequently found that a water-soluble azo compound represented by a certain formula, and an ink composition containing the same solve the problems described above. Thus, the present invention was completed.

Accordingly, a first aspect of the present invention provides a water-soluble azo compound represented by the following formula (1) or a salt thereof:

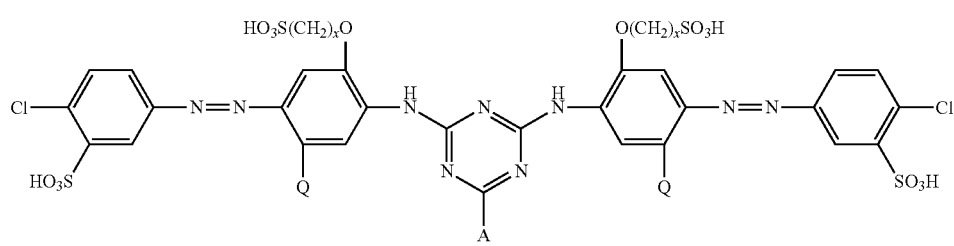

(1)

in the formula (1), Q represents a halogen atom; x represents an integer of 2 to 4; and the group A represents an amino group represented by the following formula (101):

(101)

in the formula (101), y represents an integer of 1 to 3.

A second aspect of the invention provides the water-soluble azo compound or a salt thereof according to the first aspect, in which in the above formula (1), Q is a chlorine atom; and x is 3.

A third aspect of the invention provides the water-soluble azo compound or a salt thereof according to the first aspect, in which the water-soluble azo compound represented by the above formula (1) is represented by the following formula (2):

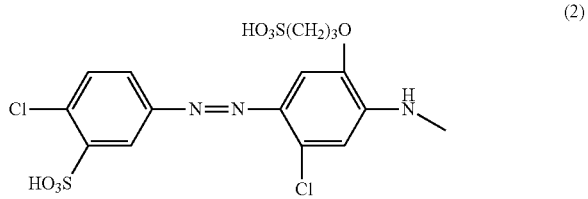

(2)

-continued

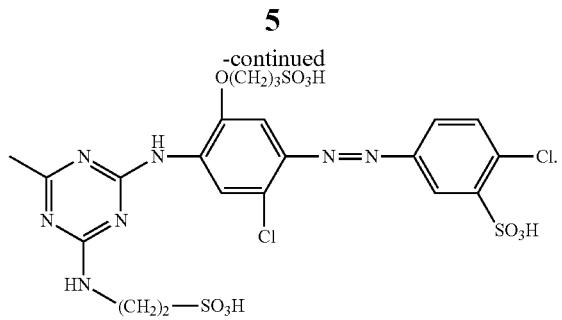

A fourth aspect of the invention provides an ink composition containing the water-soluble azo compound or a salt thereof according to the first aspect.

A fifth aspect of the invention provides the ink composition according to the fourth aspect further containing a water-soluble organic solvent.

A sixth aspect of the invention provides the ink composition according to the fourth aspect, in which the ink composition is utilized in ink jet recording.

A seventh aspect of the invention provides an ink jet recording method including discharging ink droplets in response to recording signals using the ink composition according to the fourth aspect as an ink to allow the droplets to adhere onto a record-receiving material thereby executing recording.

An eighth aspect of the invention provides the ink jet recording method according to the seventh aspect, in which the record-receiving material is a communication sheet.

A ninth aspect of the invention provides the ink jet recording method according to the eighth aspect, in which the communication sheet is a plain paper or a sheet having an ink receiving layer containing a porous white inorganic substance.

A tenth aspect of the invention provides a colored body which was colored with any one of:

(a) the water-soluble azo compound or a salt thereof according to the first aspect;

(b) an ink composition containing the water-soluble azo compound or a salt thereof according to the first aspect; and (c) an ink composition containing the water-soluble azo compound or a salt thereof according to the first aspect and a water-soluble organic solvent.

An eleventh aspect of the invention provides a colored body in which the coloring was carried out with the ink jet recording method according to the seventh aspect.

A twelfth aspect of the invention provides an ink jet printer equipped with a vessel containing the ink composition according to the fourth aspect.

Effects of the Invention

The water-soluble azo compound represented by the above formula (1) or a salt thereof of the present invention is characterized by having high solubility in water, and having favorable filterability on, for example, membrane filters, in the step of producing an ink composition of the present invention containing the compound or salt thereof. Additionally, images recorded with the ink composition of the present invention containing the compound of the present invention has superior balance between chroma saturation and ozone gas resistance. Accordingly, the water-soluble azo compound of the present invention represented by the formula (1) or a salt thereof, and an ink composition containing the same are extremely useful for applications as inks for various fields of recording, particularly applications as inks for ink jet recording.

PREFERRED MODE FOR CARRYING OUT THE INVENTION

The present invention is explained in detail below.

The water-soluble azo compound represented by the above formula (1) or a salt thereof of the present invention is a water-soluble yellow coloring matter. Unless otherwise stated in particular herein, acidic functional groups such as sulfo groups are represented in the form of their free acids. Although the present invention involves a water-soluble azo compound represented by the formula (1) or a salt of the compound as described above, description of both terms such as "compound or salt thereof", etc., for every appearance would make the specification complicated. Thus, in order to avoid complexity, unless otherwise particularly stated, "(water-soluble azo) compound or a salt thereof" in the following is expediently referred to merely as "(water-soluble azo) compound" and includes the compound and salt.

The compound of the present invention is represented by the above formula (1).

In the formula (1), Q represents a halogen atom. Specific examples of the halogen atom include a fluorine atom, a chlorine atom, a bromine atom, and an iodine atom, more preferably a fluorine atom or a chlorine atom, and particularly preferably a chlorine atom.

In the formula (1), x represents an integer of 2 to 4, and preferably 3.

In the formula (1), the group A represents an amino group represented by the formula (101). In the formula (101), y represents an integer of 1 to 3, preferably 2.

With respect to Q, W, x, and y, compounds in which preferable options are combined are more preferred, and compounds in which preferable options and particularly preferable options are combined are still more preferred.

Among the water-soluble azo compounds of the present invention represented by the above formula (1), a particularly preferable compound is a compound represented by the formula (2).

The compound of the present invention represented by the above formula (1) can be produced, for example, as in the following. It is to be noted that Q, x, and y suitably used in the following formula (AA) to formula (F) mean similarly to the definitions in the above formula (1) or formula (101), respectively.

The compound represented by the following formula (AA) obtained according to the method disclosed in Japanese Unexamined Patent Application, Publication No. 2004-75719 using 2-amino-4-halogenophenol, a commercially available product, as a basic material is converted into a methyl-ω-sulfonic acid derivative represented by the following formula (B) using sodium bisulfite and formalin. Next, 5-amino-2-chlorobenzenesulfonic acid represented by the following formula (C) is diazotized by a routine method, and the product is subjected to a coupling reaction at a reaction temperature of 0 to 15° C. and a pH of 2 to 4 with the methyl-ω-sulfonic acid derivative represented by the following formula (B) obtained above, and subsequently subjected to a hydrolyzing reaction at a reaction temperature of 80 to 95° C. and a pH of 10.5 to 11.5 to obtain a compound represented by the following formula (D).

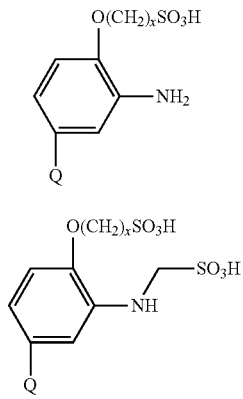
(AA)

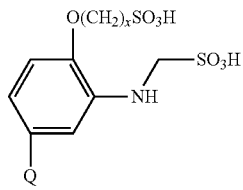
(B)

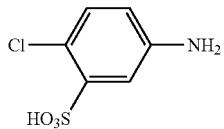
(C)

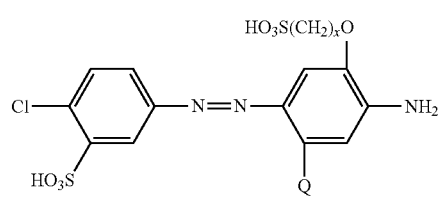
(D)

Subsequently, the compound (2 equivalents) represented by the above formula (D) is condensed with cyanuric halide (1 equivalent), for example, cyanuric chloride (1 equivalent) at a reaction temperature of 15 to 45° C. and at a pH of 5 to 8 to obtain a compound represented by the following formula (E).

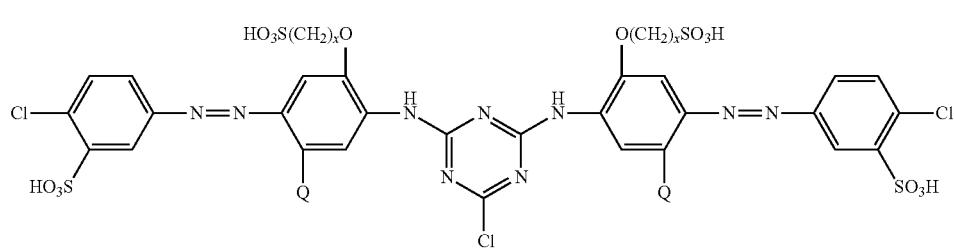
(E)

The compound of the present invention represented by the above formula (1) can be obtained by further substituting a chlorine atom on a triazine ring in the obtained compound represented by the above formula (E) with an amine represented by the following formula (F) which corresponds to the group A under a condition of a reaction temperature of 75 to 90° C. and a pH of 7 to 9.

(F)
$$H-N{\overset{H}{\underset{(CH_2)_y-SO_3H}{}}}$$

Specific examples of the amine of the above formula (F) include aminomethylsulfonic acid, taurine, and homoraurine.

Specific examples of the compound of the present invention represented by the above formula (1) are presented in Table 1 below, but the present invention is not limited thereto. It is to be noted that Q, x, and y in Table 1 correspond to Q, x, and y in the above formula (1) or (101), respectively.

TABLE 1

| Compound No. | Q | x | y | Structural formula |
|---|---|---|---|---|
| 1 | Cl | 2 | 2 | 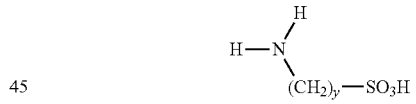 |

TABLE 1-continued
| Compound No. | Q | x | y | Structural formula |
|---|---|---|---|---|
| 2 | Cl | 3 | 2 | 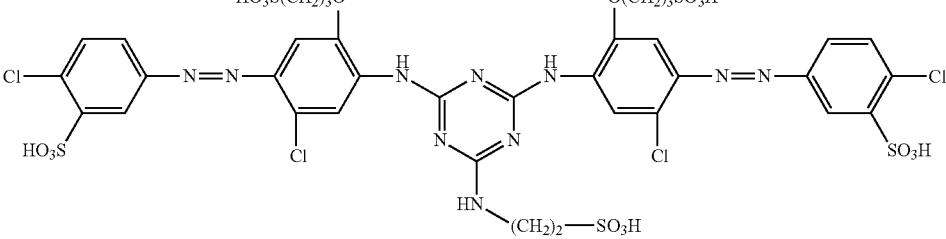 |
| 3 | Cl | 4 | 2 | 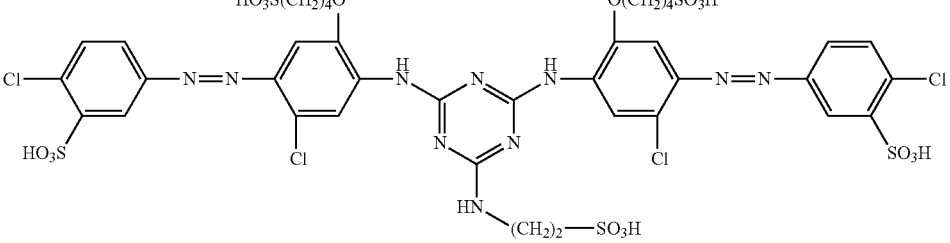 |
| 4 | Br | 3 | 2 | 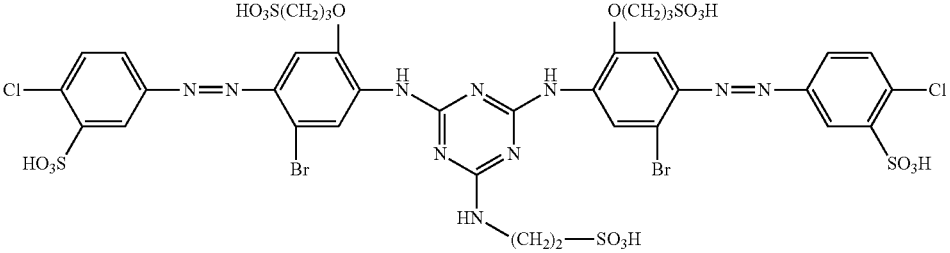 |
| 5 | F | 3 | 2 | 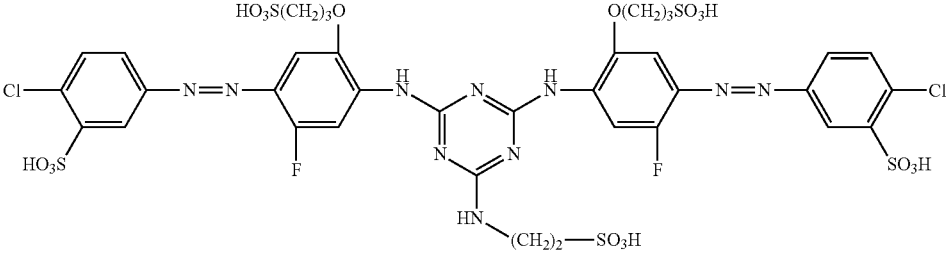 |
| 6 | I | 3 | 2 | 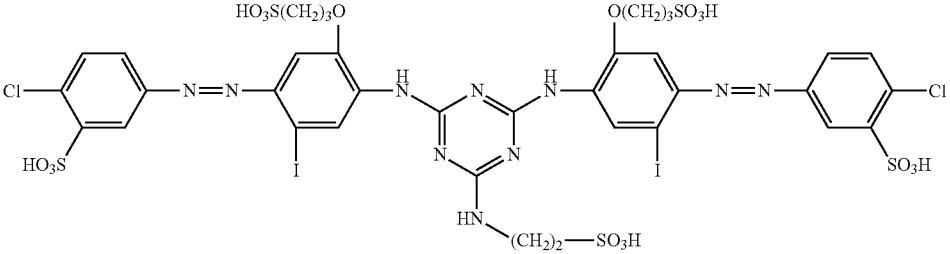 |
| 7 | Cl | 3 | 1 | 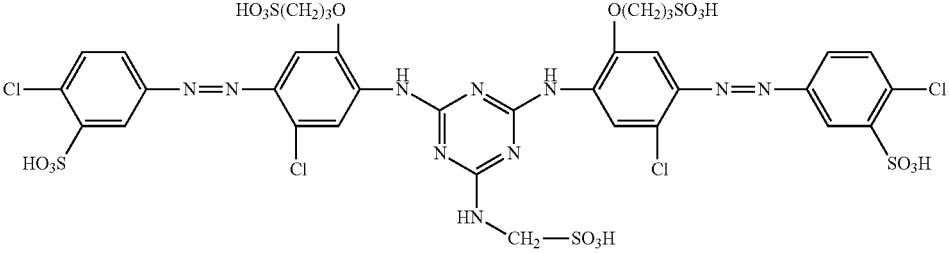 |

TABLE 1-continued

| Compound No. | Q | x | y | Structural formula |
|---|---|---|---|---|
| 8 | Cl | 3 | 3 | 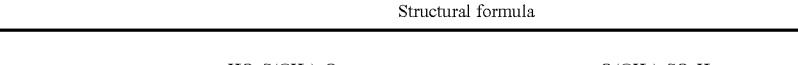 |

The compound represented by the above formula (1) is present in the form of either a free acid or a salt thereof. The salt of the compound represented by the above formula (1) may be a salt with an inorganic or organic cation. Specific examples of the inorganic cation salt include alkali metal salts, for example, lithium salts, sodium salts, potassium salts; and ammonium salts ($NE_41$. Furthermore, the organic cation salt may include, for example, a quaternary ammonium salt represented by the following formula (3), but not limited thereto.

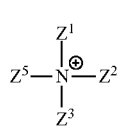 (3)

In the above formula (3), $Z^1$ to $Z^4$ each independently represent a hydrogen atom, a C1-C4 alkyl group, a hydroxy(C1-C4)alkyl group, or a hydroxy(C1-C4)alkoxy(C1-C4)alkyl group, and at least one of $Z^1$ to $Z^4$ is a group other than a hydrogen atom.

Wherein, examples of the C1-C4 alkyl group in $Z^1$ to $Z^4$ include methyl, ethyl, and the like. Similarly, examples of the hydroxy(C1-C4)alkyl group include hydroxymethyl, hydroxyethyl, 3-hydroxypropyl, 2-hydroxypropyl, 4-hydroxybutyl, 3-hydroxybutyl, 2-hydroxybutyl, and the like. Similarly, examples of the hydroxy(C1-C4)alkoxy(C1-C4)alkyl group include hydroxyethoxymethyl, 2-hydroxyethoxyethyl, 3-(hydroxyethoxy)propyl, 3-(hydroxyethoxy)butyl, 2-(hydroxyethoxy)butyl, and the like.

Among the aforementioned salts, preferable salts include alkali metal salts such as sodium, potassium and lithium salts; organic quaternary ammonium salts such as monoethanolamine, diethanolamine, triethanolamine, monoisopropanolamine, diisopropanolamine and triisopropanolamine salts; ammonium salts; and the like. Of these, more preferred are lithium salts, sodium salts, and ammonium salts.

As would be apparent to persons skilled in the art, salts or free acids of the compound represented by the above formula (1) can be easily obtained with the following method and the like.

A sodium salt, etc., of the compound represented by the above formula (1) can be obtained as a wet cake by isolating by filtration of a solid deposited by a method such as, for example: a method which includes adding, e.g., a water-soluble organic solvent such as acetone or C1-C4 alcohol to a reaction liquid after completing the reaction in the final step of the synthesis reaction of the compound represented by the above formula (1), or to an aqueous solution containing a salt of the compound represented by the formula (1); a method which includes permitting salting-out by adding sodium chloride; or the like.

Also, after thus obtained wet cake of the sodium salt is dissolved in water, the pH of the solution is adjusted appropriately by adding an acid such as hydrochloric acid, and the deposited solid is isolated by filtration. Accordingly, a free acid of the compound represented by the above formula (1), or a mixture containing a sodium salt and a free acid of the compound represented by the formula (1), i.e., the compound converted into a sodium salt in part, can be also obtained. Alternatively, after thus obtained wet cake of the sodium salt or a dry solid thereof is dissolved in water, thereto is added an ammonium salt such as ammonium chloride, and the pH of the solution is adjusted appropriately, for example, to a pH of 1 to 3, by adding an acid such as hydrochloric acid. An ammonium salt of the compound represented by the above formula (1) can be obtained by isolating thus deposited solid by filtration. By appropriately adjusting the amount of ammonium chloride added or/and the pH, a mixture containing an ammonium salt of the compound represented by the formula (1) with a sodium salt of the compound represented by the formula (1); or a mixture containing a free acid and an ammonium salt of the compound represented by the formula (1); and the like can be also obtained.

Alternatively, as described later, a free acid solid can be directly obtained by adding a mineral acid (for example, hydrochloric acid, sulfuric acid or the like) to the reaction liquid after completing the reaction. In this regard, the wet cake of the free acid of the compound represented by the formula (1) is added to water followed by stirring, and then thereto may be added, for example, potassium hydroxide; lithium hydroxide; aqueous ammonia; or hydroxide of an organic quaternary ammonium represented by the formula (3); or the like to permit production of a salt. Accordingly, a potassium salt; a lithium salt; an ammonium salt; a quaternary ammonium salt; or the like, that corresponds to each added compound can be obtained. By regulating the number of moles of the aforementioned salt added with respect to the number of moles of the free acid, preparation of, for example: mixed salts of a lithium salt and a sodium salt, etc.; alternatively, mixed salts of a lithium salt, a sodium salt, and an ammonium salt, etc. is also enabled. The salt of the compound represented by the above formula (1) may have varying physical properties such as solubility, or performances of the inks when used as an ink, depending on the type of the salt thereof. Therefore, it is also preferred to select the type of the salt to meet intended performances of the ink, and the like.

The compound of the present invention represented by the above formula (1) can be isolated in the form of a solid free acid by adding a mineral acid such as hydrochloric acid following completing the final step of the synthesis reaction, and inorganic salts such as e.g., sodium chloride and sodium sulfate contained as impurities (i.e., inorganic impurities) can be removed by washing the obtained solid free acid with water or acidic water such as aqueous hydrochloric acid, or the like. The free acid of the compound of the present invention obtained as described above in the form of a wet cake or a dry solid provided as mentioned in the foregoing, may be subjected to a treatment with a desired inorganic or organic base in water, whereby a solution of the corresponding salt of the compound can be obtained. The inorganic base includes, for example, hydroxides of an alkali metal such as lithium hydroxide, sodium hydroxide and potassium hydroxide; carbonates of an alkali metal such as lithium carbonate, sodium carbonate and potassium carbonate; or ammonium hydroxide (aqueous ammonia), and the like. Examples of the organic base include organic amine corresponding to the quaternary ammonium represented by the above formula (3), for example, alkanolamines such as diethanolamine and triethanolamine, and the like, but not limited thereto.

The compound of the present invention is suited for staining of natural and synthetic fiber materials or blended fabric products, as well as for production of compositions of inks for ink jet recording, and writing inks. For example, a reaction liquid after completing the reaction in the final step in the synthesis reaction of the compound of the present invention represented by the above formula (1) may be also used directly for producing an ink composition of the present invention. However, after isolating the compound by, for example, the aforementioned method, or drying the reaction liquid by spray drying or the like, the resulting compound can be used to prepare an ink composition.

The ink composition of the present invention is prepared by dissolving the compound represented by the above formula (1) in water or a mixed solution (may be also referred to as "aqueous medium") of water and a water-soluble organic solvent (organic solvent that is miscible with water), and adding thereto an ink preparation agent as needed. When the ink composition is used as an ink for an ink jet printer, the content of inorganic matter such as metal cation chlorides, for example, sodium chloride etc., and sulfuric acid salts, for example, sodium sulfate etc., contained as impurities is preferably as low as possible. In this regard, the total content of, for example, sodium chloride and sodium sulfate accounts for about no greater than 1% by mass in the total mass of the compound represented by the formula (1), and the lower limit may be 0% by mass, i.e., no greater than the detection limit of the analytical instrument. A method for the production of the compound including less inorganic impurities includes, for example: a method with a reverse osmotic membrane well-known per se; a method which includes adding a dried matter or wet cake of the compound of the present invention to, for example, a water-soluble organic solvent such as acetone or a C1-C4 alcohol (e.g., methanol, ethanol, isopropanol, etc.), or a water-soluble organic solvent containing water, and subjecting the mixture to suspension purification or crystallization; and the like. A desalination treatment or the like may be carried out with any of these methods.

The ink composition of the present invention contains the compound represented by the above formula (1) in an amount of usually 0.1 to 20% by mass, preferably 1 to 10% by mass, and more preferably 2 to 8% by mass in the total mass of the ink composition.

The ink composition of the present invention is prepared with water as a medium, and may appropriately contain a water-soluble organic solvent and an ink preparation agent as needed in a range which does not deteriorate the effects of the present invention.

The water-soluble organic solvent is used with the intention of achieving functions such as dissolution of the dye; prevention of the composition from drying (maintaining the wet state); adjustment of the viscosity of the composition; promotion of permeation of the coloring matter into the record-receiving material; adjustment of the surface tension of the composition; defoaming of the composition; and the like, and thus it is preferred that the water-soluble organic solvent is contained in the ink composition of the present invention.

The ink preparation agent includes well-known additives such as, for example, a preservative and fungicide, a pH adjusting agent, a chelating agent, a rust-preventive agent, an ultraviolet ray absorbing agent, a viscosity adjusting agent, a dye solubilizer, a discoloration-preventive agent, a surface tension adjusting agent, and a defoaming agent.

The content of the water-soluble organic solvent is 0 to 60% by mass, and preferably 10 to 50% by mass relative to the total mass of the ink composition of the present invention, whereas the ink preparation agent may be used in an amount of 0 to 20% by mass, and preferably 0 to 15% by mass relative to the total mass of the ink composition of the present invention. In the ink composition of the present invention, the remaining component other than the compound represented by the above formula (1), the water-soluble organic solvent, and the ink preparation agent is water.

The water-soluble organic solvent may be, for example: a C1-C4 alcohol such as methanol, ethanol, n-propanol, isopropanol, n-butanol, isobutanol, secondary butanol and tertiary butanol; an amide such as N,N-dimethylformamide and N,N-dimethylacetamide; heterocyclic ketone such as 2-pyrrolidone, N-methyl-2-pyrrolidone, hydroxyethyl-2-pyrrolidone, 1,3-dimethyl imidazolidin-2-one and 1,3-dimethyl-hexahydropyrimid-2-one; ketone or a keto alcohol such as acetone, methylethylketone and 2-methyl-2-hydroxypentan-4-one; a cyclic ether such as tetrahydrofuran and dioxane; a mono-, oligo-, or poly-alkylene glycol or thioglycol having a (C2-C6)alkylene unit such as ethylene glycol, 1,2- or 1,3-propylene glycol, 1,2- or 1,4-butylene glycol, 1,6-hexylene glycol, diethylene glycol, triethylene glycol, tetraethylene glycol, dipropylene glycol, polyethylene glycol, polypropylene glycol and thiodiglycol; polyol (preferably triol) such as trimethylolpropane, glycerin and hexane-1,2,6-triol; (C1-C4) monoalkyl ether of a polyhydric alcohol such as ethylene glycol monomethyl ether, ethylene glycol monoethyl ether, diethylene glycol monomethyl ether, diethylene glycol monoethyl ether, diethylene glycol monobutyl ether (butylcarbitol), triethylene glycol monomethyl ether and triethylene glycol monoethyl ether; γ-butyrolactone, dimethyl sulfoxide, and the like.

It is to be noted that the water-soluble organic solvent described above also includes a substance that is solid at ambient temperatures such as, for example, trimethylolpropane, etc. However, the substance, etc., exhibits solubility in water even if it is solid, and an aqueous solution containing the substance, etc., has properties similar to those of water-soluble organic solvents and can be used with the intention of achieving the same functions as the water-soluble organic solvents. Therefore, also such solid substances are expediently included in the category of "water-soluble organic solvent" herein, as long as they can be used with the intention of achieving the functions as described above.

As the water-soluble organic solvent, preferable examples include isopropanol, glycerin, mono-, di-, or tri-ethylene glycol, dipropylene glycol, 2-pyrrolidone, hydroxyethyl-2-pyrrolidone, N-methyl-2-pyrrolidone, trimethylolpropane, and butylcarbitol, whereas more preferable examples include isopropanol, glycerin, diethylene glycol, 2-pyrrolidone, N-methyl-2-pyrrolidone, and butylcarbitol. These water-soluble organic solvents are used either alone or as a mixture.

The aforementioned preservative and fungicide may include, for example, a compound of organic sulfur based, organic nitrogen sulfur based, organic halogen based, haloallyl sulfone based, iodopropargyl based, N-haloalkylthio based, benzothiazole based, nitrile based, pyridine based, 8-oxyquinoline based, isothiazoline based, dithiol based, pyridineoxide based, nitropropane based, organic tin based, phenol based, quaternary ammonium salt based, triazine based, thiadiazine based, anilide based, adamantane based, dithiocarbamate based, brominated indanone based, benzylbromoacetate based, inorganic salt based or the like.

The organic halogen based compound may include, for example, sodium pentachlorophenol.

The pyridineoxide based compound may include, for example, sodium 2-pyridinethiol-1-oxide.

The isothiazoline based compound may include, for example, 1,2-benzisothiazolin-3-one, 2-n-octyl-4-isothiazolin-3-one, 5-chloro-2-methyl-4-isothiazolin-3-one, 5-chloro-2-methyl-4-isothiazolin-3-one magnesiumchloride, 5-chloro-2-methyl-4-isothiazolin-3-one calciumchloride, 2-methyl-4-isothiazolin-3-one calciumchloride, and the like.

The other preservative and fungicide may be sodium acetate, sodium sorbate, sodium benzoate, and the like, as well as trade names Proxel® (S) and Proxel® XL-2 (S) manufactured by Arch Chemical, Inc., and the like. As used herein, the superscript notation of "®" means a registered trademark.

The pH adjusting agent may be used for the purpose of improving storage stability of the ink, and an arbitrary substance can be used as long as the pH of the ink can be controlled to fall within the range of 6.0 to 11.0. Examples of the pH adjusting agent include: alkanolamines such as diethanolamine and triethanolamine; hydroxides of an alkali metal such as lithium hydroxide, sodium hydroxide and potassium hydroxide; ammonium hydroxide; carbonates of an alkali metal such as lithium carbonate, sodium carbonate and potassium carbonate; aminosulfonic acids such as taurine; and the like.

The chelating agent may include, for example, disodium ethylenediamine tetraacetate, sodium nitrilo triacetate, sodium hydroxyethylethylenediamine triacetate, sodium diethylenetriamine pentaacetate, sodium uracil diacetate, and the like.

The rust-preventive agent may include, for example, acidic sulfite, sodium thiosulfate, ammonium thioglycolate, diisopropylammonium nitrite, pentaerythritol tetranitrate, dicyclohexylammonium nitrite, and the like.

Examples of the ultraviolet ray absorbing agent include benzophenone based compounds, benzotriazole based compounds, cinnamic acid based compounds, triazine based compounds, stilbene based compounds, and the like, and a what is generally referred to as a fluorescent whitening agent, which is a compound that absorbs an ultraviolet ray to emit fluorescence, and which is typified by a benzoxazole based compound or the like may be also used.

The viscosity adjusting agent may include in addition to the water-soluble organic solvent, a water-soluble polymer compound, and specific examples include polyvinyl alcohols, cellulose derivatives, polyamine, polyimine, and the like.

The dye solubilizer may include, for example, urea, ϵ-caprolactam, ethylene carbonate, and the like. Of these, it is preferred to use urea.

The discoloration-preventive agent is used for the purpose of improving storability of the image. As the discoloration-preventive agent, a variety of organic and metal complex based discoloration-preventive agents may be used. Examples of the organic discoloration-preventive agent include hydroquinones, alkoxyphenols, dialkoxyphenols, phenols, anilines, amines, indanes, chromanes, alkoxyanilines, heterocycles and the like, whereas examples of the metal complex include nickel complexes, zinc complexes and the like.

As the surface tension adjusting agent, surfactants may be exemplified, and examples include anionic surfactants, amphoteric surfactants, cationic surfactants, nonionic surfactants, and the like.

Examples of the anionic surfactant include alkylsulfocarboxylic acid salts, α-olefinsulfonic acid salts, polyoxyethyleneakyl ether acetic acid salts, N-acylamino acid and salts thereof, N-acylmethyltaurine salts, alkylsulfate polyoxyalkyl ether sulfuric acid salts, alkylsulfate polyoxyethylenealkyl ether phosphoric acid salts, rosin acid soap, castor oil sulfate ester salts, lauryl alcohol sulfate ester salts, alkylphenolic phosphate esters, alkylated phosphate esters, alkylarylsulfonic acid salts, diethyl sulfosuccinic acid salts, diethylhexyl sulfosuccinic acid salts, dioctyl sulfosuccinic acid salts, and the like.

Examples of the cationic surfactant include 2-vinylpyridine derivatives, poly(4-vinylpyridine) derivatives, and the like.

Examples of the amphoteric surfactant include lauryldimethylamino acetate betaine, 2-alkyl-N-carboxymethyl-N-hydroxyethylimidazolinium betaine, coconut oil fatty acid amide propyldimethylamino acetate betaine, polyoctylpolyaminoethylglycine, imidazoline derivatives, and the like.

Examples of the nonionic surfactant include: ether based surfactants such as polyoxyethylene nonylphenyl ether, polyoxyethylene octylphenyl ether, polyoxyethylene dodecyl phenyl ether, polyoxyethylene oleyl ether, polyoxyethylene lauryl ether and polyoxyethylene alkyl ether; ester based surfactants such as polyoxyethylene oleate esters, polyoxyethylene distearate esters, sorbitan laurate, sorbitan monostearate, sorbitan monooleate, sorbitan sesquioleate, polyoxyethylene monooleate and polyoxyethylene stearate; acetylene glycol (alcohol) based surfactants such as 2,4,7,9-tetramethyl-5-decyne-4,7-diol, 3,6-dimethyl-4-octyne-3,6-diol and 3,5-dimethyl-1-hexyn-3-ol; trade names Surfynol® 104, Surfynol®82 and Surfynol® 465, and Olfin® STG manufactured by Nissin Chemical Co., Ltd.; trade name Tergitol® 15-S-7 manufactured by Sigma-Aldrich Corporation; and the like.

Examples of the defoaming agent include highly oxidized oil based compounds, glycerin fatty acid ester based compounds, fluorine based compounds, silicone based compounds, and the like.

These ink preparation agents may be used either alone or as a mixture. The surface tension of the ink composition of the present invention is usually 25 to 70 mN/m, and more preferably 25 to 60 mN/m, whereas the viscosity of the ink composition is adjusted to preferably no greater than 30 mPa·s, and more preferably no greater than 20 mPa·s.

In production of the ink composition of the present invention, the order of dissolving each reagent such as additives is not particularly limited. Water employed when the composition is prepared preferably includes impurities in an amount as low as possible, and thus water such as ion exchanged water or distilled water is preferred. Furthermore, precision filtration may be carried out to remove contamination in the ink composition, as needed after the ink composition is prepared, using a membrane filter or the like. In particular, when the ink composition of the present invention is used as an ink for ink jet recording, carrying out precision filtration is preferred. The filter for use in precision filtration has a pore size of usually 1 to 0.1 μm, and preferably 0.8 to 0.1 μm.

The ink composition containing the compound of the present invention is suited for use in printing, copying, marking, writing, drawing, stamping, or recording (printing), and particularly in ink jet recording. In addition, the ink composition of the present invention is less likely to be deposited as solids even though dried in the vicinity of the nozzle of recording heads of an ink jet printer, and therefore, clogging of the recording head is also less likely to occur based on the same reason.

A process for recording on a record-receiving material with the ink jet recording method of the present invention may be as in the following. More specifically, in the process, a vessel filled with the ink composition is attached at a specified position of an ink jet printer, and the recording is executed by discharging ink droplets in response to recording signals using the ink composition of the present invention as an ink to allow the droplets to adhere onto a record-receiving material. There are ink jet printers in which, for example, a piezo system utilizing mechanical vibration; a bubble jet (registered trademark) system utilizing bubbles generated by heating; or the like is adopted. The ink jet recording method of the present invention can be employed according to any system.

In some cases, two kinds of inks containing the same coloring matter are loaded in one ink jet printer for the purpose of obtaining a higher definition image. The difference between these two kinds of inks is the content of the coloring matter, and one ink having a higher content and another ink having a lower content are used as an ink set. The ink composition of the present invention may be used as such an ink set. Also, one of the ink set may contain the ink composition of the present invention, whereas another may contain a well-known ink (composition).

The ink composition of the present invention may be provided as a yellow ink composition containing the compound of the present invention and a well-known yellow coloring matter in the range not to inhibit the effects achieved by the present invention, for the purpose of fine adjustment of the hue and the like. In addition, the compound of the present invention may be also used for applications in color conditioning of other colors, for example, of a black ink, or for the purpose of preparing a red ink or a green ink by using in combination with a magenta coloring matter or a cyan coloring matter. Furthermore, each ink of magenta and cyan, as well as if necessary, green, blue (or violet), red, black and the like may be used in combination with the ink composition of the present invention for the purpose of obtaining a full color recorded image. In this case, the ink of each color may be filled in each vessel, and the vessels may be attached at a specified position of the ink jet printer and then used.

The record-receiving material for use in the ink jet recording method of the present invention may include, for example, a communication sheet such as a paper or film, a fiber or cloth (cellulose, nylon, wool, etc.), a leather, a base material for color filters and the like, and a communication sheet is preferred. The communication sheet is not particularly limited, and not only plain paper, but also paper subjected to a surface treatment may be used, specifically, paper, synthetic paper, films and the like having an ink receiving layer provided on the base material.

The ink receiving layer has a function of absorbing the ink and accelerating the drying thereof. The ink receiving layer is provided by, for example: a method in which a cation based polymer is impregnated in or coated on the aforementioned base material; a method in which inorganic fine particles that can absorb a coloring matter in an ink are coated on the surface of the aforementioned base material together with a hydrophilic polymer such as polyvinyl alcohol or polyvinylpyrrolidone. The material entity of the inorganic fine particles that can absorb a coloring matter in an ink may include porous silica, alumina sol, special ceramics, and the like.

Such communication sheets having an ink receiving layer are generally referred to as exclusive ink jet paper, exclusive ink jet film, glossy paper, gloss film, and the like. Examples of typical commercially available products of the communication sheet having an ink receiving layer include trade names: Professional Photo Paper, Canon Photo Paper Glossy Pro (Platinum Grade) and Glossy Gold manufactured by Canon, Inc.; trade names: Photo Paper CRISPIA (Super Glossy), and Photo Paper (Glossy) manufactured by Seiko Epson Corporation; trade name: Advanced Photo Paper (Glossy) manufactured by Hewlett-Packard Japan, Ltd.; trade name: KASSAI SHASHIN-SHIAGE Pro manufactured by FUJIFILM Corporation; trade name: Photo Glossy Paper BP71G manufactured by Brother Industries, Ltd.; and the like.

Further, the plain paper means a paper which is not provided with an ink receiving layer in particular, and a variety of plain paper has been available in the market depending on their intended use. Of commercially available plain paper, examples for ink jet printing include: Plain paper with high quality on both faces (manufactured by Seiko Epson Corporation); PB PAPER GF-500 (manufactured by Canon, Inc.); Multipurpose Paper, All-in-one Printing Paper (manufactured by Hewlett Packard Co.); and the like. Additionally, plane paper copy (PPC) paper and the like for which the intended use is not particularly limited to ink jet recording is also included in the plain paper.

The colored body of the present invention means a substance which was colored with any one of: (a) the water-soluble azo compound of the present invention; (b) the ink composition of the present invention containing the compound; and (c) the ink composition of the present invention containing the compound and a water-soluble organic solvent. The substance colored is not particularly limited, and may include for example, the aforementioned record-receiving materials, and the like, but not limited thereto. Preferably the aforementioned record-receiving materials colored may be exemplified. Although not particularly limited, the coloring method of the substance may include, for example, printing methods such as a dip dyeing method, a textile printing method and a screen printing, as well as the ink jet recording method of the present invention, and the like, but the ink jet recording method of the present invention is preferred. Among the aforementioned colored bodies, a colored body which was colored by the ink jet recording method of the present invention is preferred.

The water-soluble azo compound of the present invention represented by the above formula (1) is extremely superior in solubility in water and water-soluble organic solvents. Additionally, the water-soluble azo compound is characterized by having favorable filterability on, for example, membrane filters, in the step of producing an ink composition of the present invention. The ink composition of the present invention provides yellow recorded images that are very brilliant, and having a high chroma saturation and print density, and ideal hue on record-receiving materials such as plain paper and communication sheets having an ink receiving layer. Thus, strict reproduction of photographic color images on paper is enabled. Moreover, the ink composition of the present invention exhibits extremely favorable storage stability, without solid deposition, physical property alteration, change in the hue and the like after storage for a long period of time.

Even if the ink composition of the present invention is used as an ink jet ink, deposition of solids due to drying of the ink composition in the vicinity of the nozzle hardly occurs, and clogging of the injector (recording head) can be also avoided. Also, the ink composition of the present invention does not cause alteration of physical properties even when the ink is used by recycling with a comparatively long time interval using a continuous ink jet printer, or even when intermittently used with an on-demand ink jet printer.

Still further, images recorded on a communication sheet having an ink receiving layer with the ink composition of the present invention have high chroma saturation, and have various types of favorable fastness properties such as water resistance, moisture resistance, ozone gas resistance, friction resistance and light resistance, in particular ozone gas resistance, and have superior balance between the chroma saturation and the ozone gas resistance. For this reason, superior long-term storage stability of photographic image is also achieved. Also, superior coloring properties such as chroma saturation, brightness, and print density on plain paper are attained as compared with conventional inks.

Accordingly, a water-soluble azo compound represented by the formula (1), and the ink composition of the present invention containing the same are extremely useful for applications as various types of recording inks, particularly applications as inks for ink jet recording.

EXAMPLES

Hereinafter, the present invention is more specifically described below by way of Examples, but it is not to be construed as being limited thereto. In the specification, unless otherwise stated particularly, the expressions "part" and "%" are on the basis of the mass, and the reaction temperature means an interior temperature.

With respect to some of the compounds synthesized, λmax (wavelength of maximum absorption) shows the value of measurement in an aqueous solution of pH 7 to 8.

Also, in each structural formula of the compounds obtained in the Examples, the acidic functional group such as a sulfo group is represented in the form of its free acid.

It should be noted that, solubility in water at room temperature of any of the compounds of the present invention obtained in the Examples was no less than 100 g/L.

Example 1

Step 1

5-Amino-2-chlorobenzenesulfonic acid in an amount of 20.8 parts was dissolved in 200 parts of water while adjusting the pH to 6 with sodium hydroxide, and then 7.2 parts of sodium nitrite were added thereto. After this solution was added dropwise to 200 parts of 5% hydrochloric acid at 0 to 10° C. over 30 min, the mixture was stirred at no higher than 10° C. for 1 hour to carry out a diazotization reaction, whereby a diazo reaction liquid was prepared. On the other hand, 26.6 parts of 2-(sulfopropoxy)-5-chloroaniline were dissolved in 130 parts of water while adjusting the pH to 7 with sodium hydroxide and converted into a methyl-ω-sulfonate derivative using 10.4 parts of sodium bisulfite and 8.6 parts of 35% formalin by a routine method. Thus obtained methyl-ω-sulfonate derivative was added to the diazo reaction liquid prepared beforehand, and the mixture was stirred at 0 to 15° C. and a pH of 2 to 4 for 24 hrs. After the pH of the reaction liquid was adjusted to 11 with sodium hydroxide, the liquid was stirred while maintaining the same pH at 80 to 95° C. for 5 hrs, and 100 parts of sodium chloride were added to this reaction liquid for salting-out to occur, and the deposited solid was isolated by filtration to obtain 100 parts of an azo compound represented by the following formula (4) as wet cake.

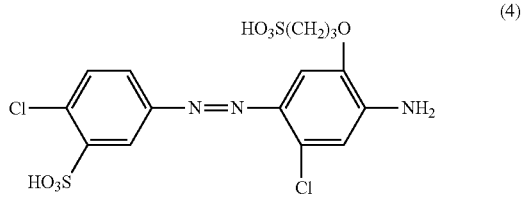

Step 2

Into 250 parts of ice water were added 0.10 parts of Leocol® TD90 (trade name, surfactant) manufactured by Lion Corporation, and the mixture was vigorously stirred, to which 3.6 parts of cyanuric chloride were added, followed by stirring at 0 to 5° C. for 30 min to obtain a suspension. Subsequently, the wet cake of the compound represented by the above formula (4) in an amount of 100 parts was dissolved in 200 parts of water, and the aforementioned suspension was added dropwise to this solution over 30 min. After completing the dropwise addition, the mixture was stirred at a pH of 6 to 8 and at 25 to 45° C. for 6 hrs. To the obtained liquid were added 37.5 parts of taurine, followed by stirring at a pH of 7 to 9 and at 75 to 90° C. for 4 hrs. After cooling the obtained reaction liquid to 20 to 25° C., 800 parts of acetone were added to this reaction liquid, followed by stirring at 20 to 25° C. for 1 hour. The deposited solid was isolated by filtration to obtain 50.0 parts of wet cake. This wet cake was dried with a hot-air dryer at 80° C. to obtain 13.5 parts of a sodium salt of the water-soluble azo compound (λmax: 408 nm) of the present invention represented by the following formula (5).

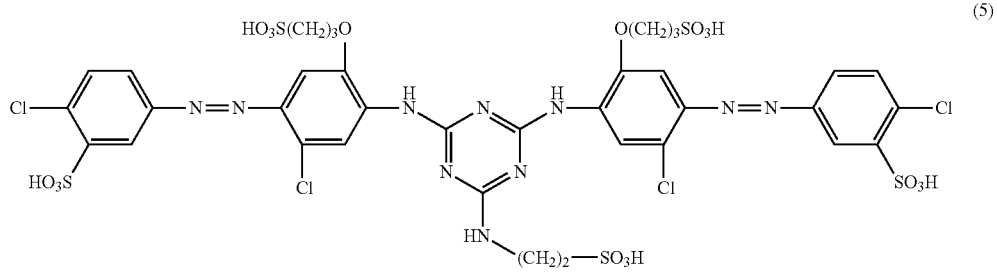

Example 2

(A) Preparation of Ink

Using the azo compound (sodium salt represented by the formula (5)) of the present invention obtained in the aforementioned Example 1 as a coloring matter, the ink composition of the present invention was obtained by mixing the blend shown in the following Table 2 to prepare a solution. Thus obtained ink composition was filtered through a 0.45 μm membrane filter to remove contaminants, whereby an ink for testing was prepared. The pH of this ink for testing was in the range of 8.0 to 9.5. In the following Table 2, the "Surfactant" employed was trade name Surfynol® 104PG50 manufactured by Nissin Chemical Co., Ltd.

TABLE 2

| Blend of ink composition | |
| --- | --- |
| Compound obtained in each Example | 3.5 parts |
| Glycerin | 5.0 parts |
| Urea | 5.0 parts |
| N-methyl-2-pyrrolidone | 4.0 parts |
| Isopropyl alcohol | 3.0 parts |
| Butylcarbitol | 2.0 parts |
| Surfactant | 0.1 parts |
| Ion exchanged water | 77.4 parts |
| Total | 100.0 parts |

Comparative Example 1

A comparative ink was prepared in a similar manner to Example 2 except that the compound represented by the following formula (6) was used in place of the compound of the present invention obtained in Example 1. The preparation of this ink is designated as Comparative Example 1. The compound used in Comparative Example 1 is disclosed in Japanese Examined Patent Application, Pubication No. S55-011708, and Japanese Unexamined Patent Application, Pubication No. 2002-285022 discloses use of the compound as an ink let ink.

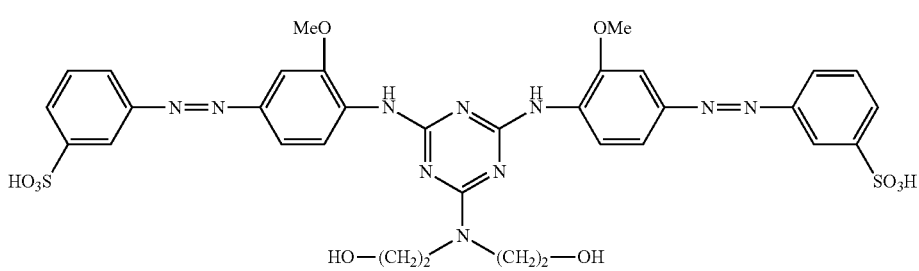

(6)

Comparative Example 2

A comparative ink was prepared in a similar manner to Example 2 except that a coloring matter disclosed in Example 1 of Patent Document 1 was used in place of the compound of the present invention obtained in Example 1. The preparation of this ink is designated as Comparative Example 2. The structural formula of the compound used in Comparative Example 2 is shown in the following formula (7).

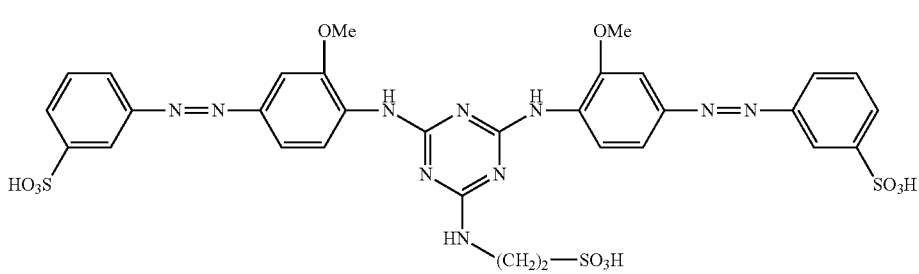

(7)

Comparative Example 3

A comparative ink was prepared in a similar manner to Example 2 except that a coloring matter disclosed in Example 1 of Patent Document 2 was used in place of the compound of the present invention obtained in Example 1. The preparation of this ink is designated as Comparative Example 3. The structural formula of the compound used in Comparative Example 3 is shown in the following formula (8).

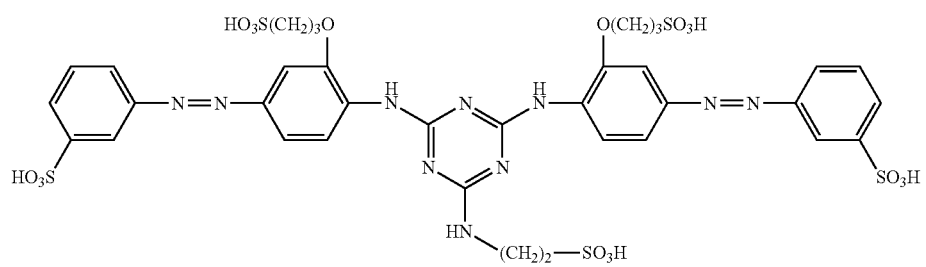

(8)

Comparative Example 4

A comparative ink was prepared in a similar manner to Example 2 except that a coloring matter disclosed in Example 1 of Patent Document 3 was used in place of the compound of the present invention obtained in Example 1. The preparation of this ink is designated as Comparative Example 4. The structural formula of the compound used in Comparative Example 2 is shown in the following formula (9).

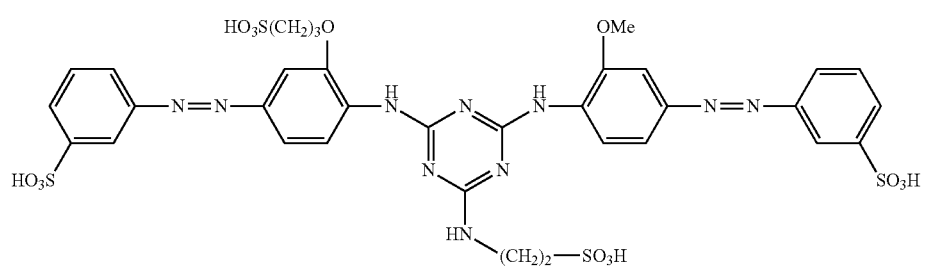

(9)

(B) Ink Jet Recording

Using an ink jet printer (manufactured by Canon, Inc., trade name: PIXUS® ip4500), ink jet recording was carried out on a few kinds of glossy paper, trade name: Canon Photo Paper Glossy Pro (Platinum Grade) manufactured by Canon, Inc. (exclusive ink jet paper) and trade names: Photo Paper CRISPIA (Super Glossy) manufactured by Seiko Epson Corporation, with each ink prepared in the aforementioned Example 2, and Comparative Examples 1 to 4. Upon ink jet recording, an image pattern was produced such that several-step gradation of the reflected density was obtained, whereby a yellow gradational recorded matter was produced. Using the thus obtained recorded matter as a test piece, various types of tests were performed.

Glossy paper 1: manufactured by Canon, Inc., trade name: Canon Photo Paper Glossy Pro (Platinum Grade)

Glossy paper 2: manufactured by Canon, Inc., trade name: Canon Photo Paper Glossy Gold Glossy paper 3: manufactured by Seiko Epson Corporation, trade name: Photo Paper CRISPIA (Super Glossy)

For the ozone gas resistance test, reflected density was determined on a part where the reflected density, i.e., D value, of the recorded matter before the test was most approximate to 1.0. For measurement of the reflected density, a colorimetric system (trade name SpectroEye®, manufactured by X-Rite Co., Ltd.) was used. The colorimetric determination was carried out under a condition of a viewing angle of 2°, and a light source of D65, with a density standard of DIN. Various test methods, and evaluation methods of the test results of the recorded image are described below.

(C) Chroma Saturation Test

With respect to a gradational part having the highest reflected density on each test piece, the value of yellow chroma saturation C* was measured with the aforementioned colorimetric system. Evaluation criteria are as in the following.

C value being no less than 110: A

C value being less than 110: B

The results are shown in Table 3 below.

(D) Ozone Gas Resistance Test

Each test piece was left to stand under a condition of: an ozone concentration of 10 ppm; a humidity of 50% RH; and a temperature of 30° C., using an Ozone Weather Meter OMS-H (manufactured by Suga Test Instruments Co., Ltd.) for 16 hrs. The colorimetric determination of the reflected density was carried on each test piece after the testing using the aforementioned colorimetric system. The residual ratio of the coloring matter was determined by calculation according to the formula of: (reflected density after test/reflected density before test)×100(%), and evaluation was made by rating on a three point scale.

Residual ratio of the coloring matter being no less than 90%:A

Residual ratio of the coloring matter being less than 90% and no less than 80%:B Residual ratio of the coloring matter being less than 80%:C The results are shown in Table 4 below.

TABLE 3

| Results of chroma saturation test | Glossy paper 1 | Glossy paper 2 | Glossy paper 3 |
|---|---|---|---|
| Example 2 | A | B | A |
| Comparative Example 1 | B | B | B |
| Comparative Example 2 | B | B | B |
| Comparative Example 3 | B | B | B |
| Comparative Example 4 | B | B | B |

TABLE 4

| Results of ozone gas resistance test | Glossy paper 1 | Glossy paper 2 | Glossy paper 3 |
|---|---|---|---|
| Example 2 | A | B | B |
| Comparative Example 1 | B | B | C |
| Comparative Example 2 | C | C | C |
| Comparative Example 3 | C | C | C |
| Comparative Example 4 | B | C | C |

From the results shown in Table 3, it can be seen that each Example of the present invention exhibits comparable or higher chroma saturation and superior brilliance, as compared with each Comparative Example.

In addition, as is evident from the results shown in Table 4, each Example of the present invention is superior to each Comparative Example in the ozone gas resistance.

Therefore, it can be seen that the water-soluble azo compound of the present invention and an ink composition of the present invention containing the same have superior balance between chroma saturation and ozone gas resistance, since they have a hue with high brilliance and are superior in ozone gas resistance.

INDUSTRIAL APPLICABILITY

The water-soluble azo compound of the present invention that is a yellow coloring matter, and a yellow ink composition of the present invention containing the same provide recorded images having a high chroma saturation. In addition thereto, they are also superior in fastness properties in various fields such as ozone gas resistance. Therefore, the compound, and an ink composition containing the compound are very useful for various types of applications in recording, particularly applications in ink jet recording.

The invention claimed is:

1. A water-soluble azo compound represented by the following formula (1) or a salt thereof:

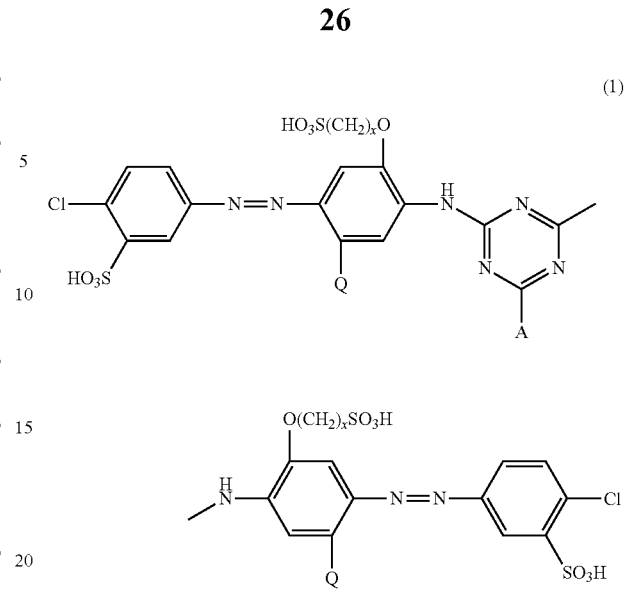

wherein, Q represents a halogen atom; x represents an integer of 2 to 4; and the group A represents an amino group represented by the following formula (101):

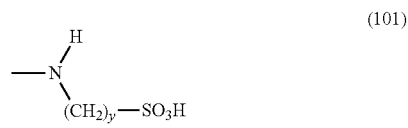

wherein, y represents an integer of 1 to 3.

2. The water-soluble azo compound or a salt thereof according to claim 1, wherein in the above formula (1), Q is a chlorine atom; and x is 3.

3. The water-soluble azo compound or a salt thereof according to claim 1, wherein the water-soluble azo compound represented by the above formula (1) is represented by the following formula (2):

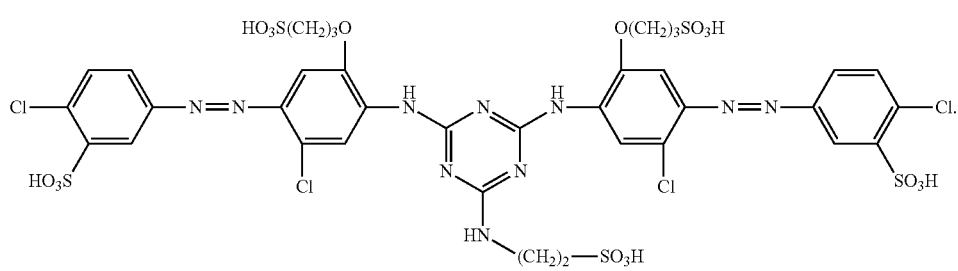

4. An ink composition comprising the water-soluble azo compound or a salt thereof according to claim 1.

5. The ink composition according to claim 4 further comprising a water-soluble organic solvent.

6. The ink composition according to claim 4, wherein the ink composition is utilized in ink jet recording.

7. An ink jet recording method comprising discharging ink droplets in response to recording signals utilizing the ink composition according to claim 4 as an ink to allow the droplets to adhere onto a record-receiving material thereby executing recording.

8. The ink jet recording method according to claim 7, wherein the record-receiving material is a communication sheet.

9. The ink jet recording method according to claim 8, wherein the communication sheet is a plain paper or a sheet having an ink receiving layer containing a porous white inorganic substance.

10. A colored body which is colored with any one of:
(a) the water-soluble azo compound or a salt thereof according to claim 1;
(b) an ink composition containing the water-soluble azo compound or a salt thereof according to claim 1; and
(c) an ink composition containing the water-soluble azo compound or a salt thereof according to claim 1 and a water-soluble organic solvent.

11. A colored body wherein the coloring was is carried out with the ink jet recording method according to claim 7.

12. An ink jet printer equipped with a vessel containing the ink composition according to claim 4.

* * * * *

UNITED STATES PATENT AND TRADEMARK OFFICE
CERTIFICATE OF CORRECTION

| | | |
|---|---|---|
| PATENT NO. | : 8,506,697 B2 | Page 1 of 1 |
| APPLICATION NO. | : 13/634798 | |
| DATED | : August 13, 2013 | |
| INVENTOR(S) | : Ryoutarou Morita | |

It is certified that error appears in the above-identified patent and that said Letters Patent is hereby corrected as shown below:

At Title Page 1 (Item 57) Abstract, Line 4, Change "inkjet" to --ink jet--.

In the Specification

At Column 1, Line 15, Change "disazo" to --diazo--.

At Column 2, Line 34, Change "lead" to --led--.

At Column 8, Line 47, Change "homoraurine" to --homotaurine--.

At Column 11, Line 24, Change "($NE_41$." to --($NH_4^+$).--.

At Column 11, Lines 31-34, Change " 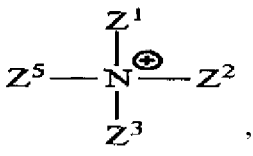 " to -- 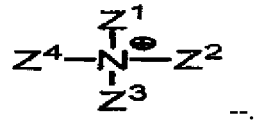 --.

At column 18, Line 32, Change "plane" to --plain--.

At Column 22, Line 20, Change "Pubication" to --Publication--.

At Column 22, Lines 21-22, Change "Pubication" to --Publication--.

At Column 22, Line 23, Change "let" to --jet--.

At Column 24, Line 42, Change "C" to --C*--.

At Column 24, Line 43, Change "C" to --C*--.

In the Claims

At Column 27, Line 19, In Claim 11, Change "was is" to --is--.

Signed and Sealed this
Sixth Day of May, 2014

Michelle K. Lee
*Deputy Director of the United States Patent and Trademark Office*